United States Patent [19]

Shao et al.

[11] Patent Number: 5,025,784

[45] Date of Patent: Jun. 25, 1991

[54] APPARATUS AND METHOD FOR DETECTING AND PROCESSING IMPEDANCE RHEOGRAM

[75] Inventors: Shuyong Shao; Jianhua Feng; Xinchao Zhang, all of Harbin, China

[73] Assignee: Harbin Polytechnic University, Harbin, China

[21] Appl. No.: 240,620

[22] Filed: Sep. 6, 1988

[30] Foreign Application Priority Data

Sep. 5, 1987 [CN] China .................. 87106212

[51] Int. Cl.$^5$ ............................................. A61N 1/00
[52] U.S. Cl. ............................ 128/419 PG; 128/734; 128/700
[58] Field of Search ............ 128/419 D, 419 PG, 734, 128/696, 700, 702, 716

[56] References Cited

U.S. PATENT DOCUMENTS

| | | | |
|---|---|---|---|
| 4,450,527 | 5/1984 | Sramek | 128/734 |
| 4,649,932 | 3/1987 | Smith | 128/734 |
| 4,733,670 | 3/1988 | Hays et al. | 128/734 |
| 4,785,812 | 11/1988 | Pihl et al. | 128/419 D |
| 4,823,797 | 4/1989 | Heinze et al. | 128/734 |

*Primary Examiner*—Francis Joworski
*Assistant Examiner*—George Manuel

[57] ABSTRACT

An apparatus and method for detecting and processing an impedance rheogram includes a constant current source with output electrodes, an impedance signal detecting circuit having detecting electrodes, an ECG signal detecting circuit having detecting electrodes, a signal processing circuit and an output device. The impedance signal detecting circuit and ECG signal detecting circuit respectively, defect the impedance signal and ECG signal, the signal whereby processing circuit divides the impedance signal into cycles according to an R wave sequence, then performs linear interpolating for each cycle and in-phase superposing-averaging for a certain number of cycles, and restores the impedance waveform according to a predetermined number of interpolating points used for each cycle, so as to automatically trace arrhythmia and eliminate respiration interference to the impedance rheogram.

9 Claims, 5 Drawing Sheets

APPARATUS AND METHOD FOR DETECTING AND PROCESSING IMPEDANCE RHEOGRAM

FIELD OF THE INVENTION

The present invention relates to an apparatus and method for detecting and processing an impedance rheographic signal $\Delta Z$ and, more particularly, to an apparatus and method which detects simultaneously the impedance signal and electrocardiogram (ECG) signal from a subject, then performs linear interpolating and in-phase superposing-averaging of the detected impedance signal according to the cycle of the ECG signal so to eliminate interference to the impedance rheogram by the subject's respiration, thus detecting the impedance rheogram of different organs while keeping the subject in free respiration.

BACKGROUND OF THE INVENTION

In detecting impedance rheogram (plethysmogram), a small and high-frequency constant current is applied to a part or an organ of a subject's body, and at the same time, the variation of the electric impedance of the part or organ caused by the change of blood volume in a blood vessel during a heart beat process is detected and recorded, and the recorded waveforms are called the impedance rheogram. In practice, the rheograms detected at different part or organs are respectively called rheocardiogram, pulmonary rheogram, rheohepatogram, rheoencephalogram, and the like. The present invention relates to the former three kinds of rheogram which are apt to be interfered with by a subject's respiration.

When the impedance rheograms of heart, lung and liver are detected by conventional means, the variation of impedance will also be caused by the change of air volume in the lungs during respiration, thus the detected results of the impedance rheogram will be seriously distorted. In order to avoid respiration interference, the subjects are required to hold their respiration during detection, but this requirement is almost impossible for those having serious heart problems, for those who are respiration problems, unconscious or for young babies. Therefore, the conventional apparatus and methods can not be used on these subjects.

Besides the respiration interference, the detection of the impedance rheogram is also apt to be interfered with by many internal factors (such as subject's body movements electromyographic and electrocardiographic signals, etc) as well as external factors (such as environmental interference and instrument noise). All of these factors will reduce the reliability of the detection results.

In an article entitled "Microprocessor Impedance Rheogram System" by Liu Ying, in APPLICATION OF ELECTRONIC TECHNOLOGY, volume 1, 1984, PP 17-19, there is disclosed a system for eliminating respiration interference of the differential impedance rheocardiogram dz/dt by way of digital superposing. However, the superposing thereof is done according to a constant sampling frequency, which is neither adequate for those having arrhythmia nor for those having heart rate change during detection. It has been proved by clinical data that many healthy people's heart rate is changed under free respiration, and serious arrhythmia may be found in many patients having heart problems, and all these will certainly change the cyclic waveforms of the impedance rheogram. Under such situations, the superposition processing on the basis of sampling with a constant time interval will cause significant errors, thus rendering it useless in clinical practice.

SUMMARY OF THE INVENTION

One object of the present invention is to provide an apparatus for detecting and processing an impedance rheogram, which is capable of automatically tracing arrhythmia to eliminate the respiration interference. By using this apparatus, the impedance rheogram may be detected without any interruption of the subject's respiration, and the respiration interference is overcome by tracing the change of subject's heart rhythm, so that the useful information about the subject's physiological status may be obtained.

Another object of the present invention is to provide a method for processing the impedance signals detected under free respiration, wherein the respiration interference contained in the impedance rheographic waveforms is eliminated by tracing the change of heart rhythm, so that waveforms reflecting the change of blood volume in the detected portion are obtained.

Yet another object of the present invention is to provide an apparatus and a method for eliminating interferences caused by many internal and external factors during the detection of impedance rheogram, to thereby improve the reliability of the detected results and to increase the application thereof in practice.

The apparatus and method of the present invention are adapted for detecting impedance rheocardiogram, impedance pulmonary rheogram and impedance rheohepatogram for all kinds of patients, including those having arrhythmia, under free respiration. They are also adapted for monitoring the change of the impedance rheographic waveforms during a relatively long period of time to find out the dynamic trend thereof.

One embodiment of the apparatus for detecting and processing impedance rheogram according to the present invention comprises: a constant current source which applies a constant current with a frequency in the range of 20-100 $KH_z$ and an amplitude of less than 2 mA to a subject's body part via a pair of current output electrodes; an impedance signal detecting circuit which detects, via a pair of voltage detecting electrodes, the impedance variation at the detected body part under the effect of the constant current, then amplifies and filters the detected impedance signal; an ECG signal detecting circuit which detects, via ECG electrodes, at least one lead ECG signals and generates a pulse sequence corresponding to the R waves of the ECG signal; a digital signal processing circuit which provides a parallel input of the impedance signal, the ECG signal and the R wave sequence, performs linear interpolation processing on the digitized impedance and ECG signals for a predetermined number of interpolating points with R wave sequence as the cyclic reference, then performs in-phase superposing-averaging processing on the impedance signal for a certain number of cycles thereof and restores the waveform according to the interpolating points, and provides the processed impedance signal and ECG signal synchronously as output; and an output device for displaying and recording the output results.

The method for detecting and processing impedance rheogram according to the present invention comprises the following steps:

1) applying a constant current with a frequency in the range of 20–100 KH$_z$ and an amplitude of less than 2 mA to a subject's selected body part;

2) detecting simultaneously the impedance signal of the selected body part and the subject's ECG signal, and generating an R wave sequence therefrom;

3) converting synchronously the impedance signal and ECG signal into digital form and sampling the same with a constant time interval;

4) dividing the impedance signal into cycles according to the R wave sequence;

5) performing linear interpolation to the sampling results in each cycle of the impedance signal to divide each cycle evenly by a predetermined number of interpolating points with each of the points corresponding to a certain phase of the cycle;

6) performing in-phase superposing-averaging processing on each of the interpolating points within a cycle with a predetermined number of adjacent cycles and restoring the impedance waveform according to the interpolating points; and 7) providing the impedance waveform and ECG waveform as output for displaying and recording via an output device.

In the apparatus and method of the present invention, the respiration interference to the impedance rheogram is eliminated by a superposing-averaging processing which automatically traces the heart rhythm and at the same time, the interferences caused by other internal and external random factors are also eliminated. Thus, the impedance rheogram of heart, lungs and liver may be detected with the subject in free respiration. Since a subject is not required to hold respiration during detection, the detected results give more information about subject's normal physiological status, and it is possible to perform a prolonged monitoring of the dynamic process. Therefore, the present invention will find a wide application in clinical and research practice.

The above-mentioned and other objects, features and advantages of the present invention will become more apparent in the following detailed descriptions of the preferred embodiment in combination with the accompanying drawings.

DETAILED DESCRIPTION OF THE PREFERRED EMBODIMENT

Figure 1:
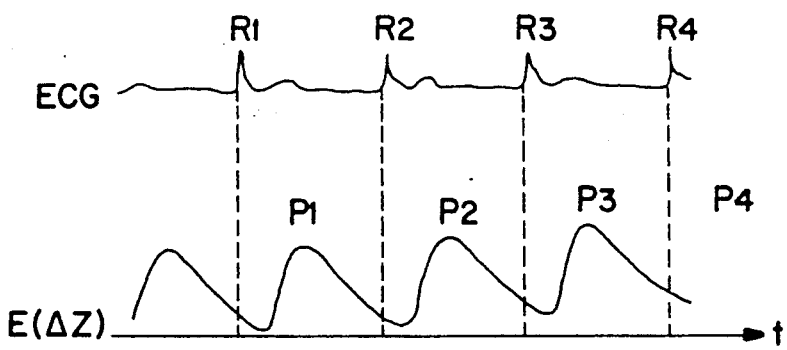
FIG. 1 shows the waveform of the impedance rheogram having no respiration interference, detected with the subject holding respiration, and the ECG waveform simultaneously detected.

Referring to FIG. 1, there is shown the impedance rheogram waveform E (Z) having no respiration interference, detected with the subject holding his breath, and the ECG waveform simultaneously detected. It can be seen in FIG. 1 that with a starting point of an R wave in the ECG signal as the reference point, the impedance rheogram may be correspondingly divided into cycles $P_1$, $P_2$, $P_3$ . . . , each of them corresponding to a cardiac cycle. When there is a change in the subject's heart rhythm, there will also be a corresponding change in the cyclic waveform of the impedance rheogram.

Since the impedance rheogram detected with the subject holding his breath is not interfered with by respiration, the relationship between the cyclic waveform of the impedance rheogram and that of the ECG signal may be seen, thus the ECG signal may be used as a reference in dividing impedance rheogram signal into cycles.

Figure 2:
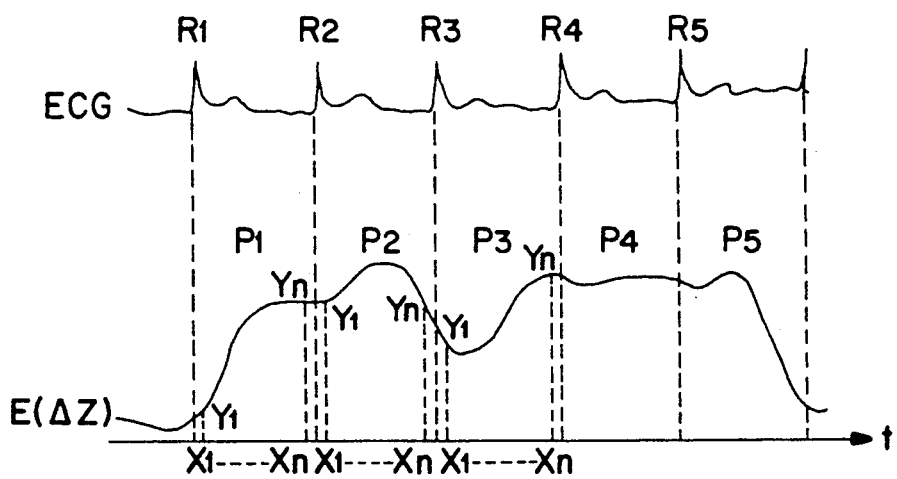
FIG. 2 shows the waveform of the impedance rheogram having respiration interference, and the ECG waveform simultaneously detected.

FIG. 2 shows the waveform of the impedance signal detected with the subject in free respiration and the waveform of the ECG signal simultaneously detected. The waveform of the impedance signal E ($\Delta$Z) consists of the impedance variation caused by the change of blood volume (impedance rheographic signal) as well as the impedance variation caused by subject's respiration (respiration interference). Because the amplitude of the impedance variation caused by respiration is 3–10 times as large as that of the impedance rheographic signal, and the fundamental frequency of the respiration signal is very close to that of the impedance rheographic signal, usually the former is one third to one fifth of the latter, and the cyclic characteristics of the impedance rheographic waveform is no longer recognizable in this composed signal. According to the conception of the present invention, the impedance rheographic component in the waveform shown in FIG. 2 is treated as a cyclic signal, while the respiratory component is treated as a random signal relative to the former one, so it can be processed as noise. Using the start points of the R waves in the ECG signal as the reference points, the impedance rheographic waveform is divided into cycles with each cycle thereof containing a complete impedance rheographic waveform. In the method according to the present invention, in order to eliminate the respiration interference in each cycle, the waveform shown in FIG. 2 is first sampled with a constant time interval A to obtain the sampling counts $K_1$, $K_2$ . . . for each cycle $P_1$, $P_2$ . . . ($P_n = AK_n$), respectively. Since the sampling time interval A is a constant, the sampling count of a cycle is different for different heart rates (i.e. the sampling count for a heart rate of 120 times per minute is one half that of a heart rate of 60 times per minute). On the other hand, when the subject has arrhythmia, the time duration for each cycle is not equal $P_1 \neq P_2$), hence the sampling count for each cycle is also not equal ($K_1 \neq K_2$). In order to perform the in-phase superposing between different cycles of the signal, a linear interpolation processing is performed to the sampling points within each cycle, so that each cycle is evenly divided into a predetermined number of interpolation points $X_1$, $X_2$ . . . $X_n$ (wherein n be 64 or 128).

The abscissa for each interpolation point on time axis is calculated according to the following equation:

$$X_n = (A \cdot K \cdot n)/64 \qquad (1)$$

Wherein,
A is the constant sampling time interval;
K is the actual sampling count in this cycle;
n is the sequence number of the interpolating point, n=1, 2, 3, ... 64

When the predetermined number of interpolating is made 128, the denominator of equation (1) should also changed into 128. When the abscissa of each interpolating point has been determined by using equation (1), the amplitudes of the impedance signal $Y_1, Y_2 ... Y_n$ corresponding to the interpolating points $X_1, X_2, ... X_n$ are calculated according to the linear interpolation equation:

$$Y_n = y_o + (Y_1 - y_o)(X_n - x_o)/(x_1 - x_o) \qquad (2)$$

Wherein,
$X_n$ is the abscissa of the interpolating point calculated by using equation (1);
$x_o$ and $x_l$ are respectively the absciassas of two sampling points which are the closest points to $X_n$ on time axis, and $x_o < X_n < x_l$, $x_1 - x_o = A$, n=1, 2, 3, ... 64;
$y_o$ and $y_l$ are the sampling values corresponding to $x_o$ and $x_l$.

By using the above equations (1) and (2), the interpolation results of each cycle may be calculated according to the sampling results of the impedance signal within the same cycle, then, no matter what the time duration of a cycle P is, it is divided into the same number of interpolating points. When the linear interpolation processing has been done for each cycle of the waveform shown in FIG. 2, the interpolation results of each cycle are superposed and averaged with the corresponding points of a number of adjacent cycles N to obtain an averaged value of the impedance signal for each point, whereby the superposing number N may be 8 or 16. Thus, the $Y_1$ of each of cycles $P_1 - P_8$ are averaged to obtain an averaged $\overline{Y}_1$, and in the same way to obtain the averaged impedance values $\overline{Y}_1, \overline{Y}_2, ... \overline{Y}_{64}$ which are plotted corresponding to the abscissas of the interpolating points $X_1, X_2 ... X_{64}$ to restore the impedance waveform in cycle $P_1$. In the same way, the waveform of $P_2$ may be restored by in-phase superposing and averaging of the values of cycles $P_2 - P_9$, and so on for the waveforms of other cycles.

Figure 3:
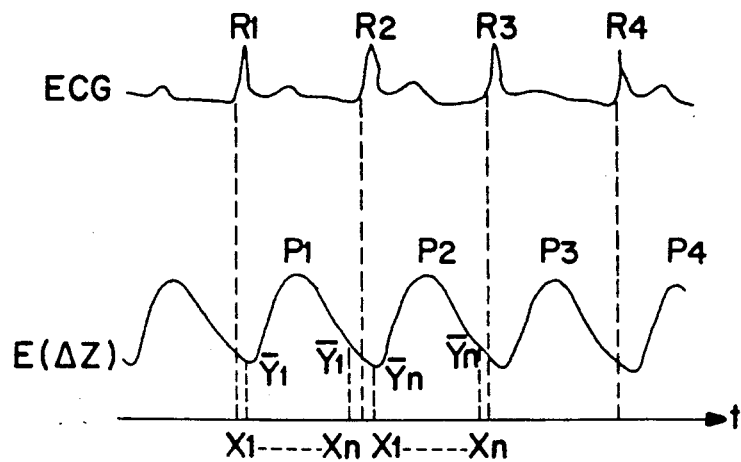
FIG. 3 shows the waveform of the impedance rheogram detected using the apparatus and method of the present invention to eliminate the respiration interference, and the ECG waveform being simultaneously detected.

FIG. 3 shows the restored waveform of the impedance signal after the processing of linear interpolation and in-phase superposing-averaging. Since the processing is done according to the cyclic features of the impedance rheographic signal, the respiration interference component is cancelled as a random interfering signal during the processing, hence the restored waveform will reflect only the cyclic features of the impedance rheographic signal. It should be pointed out that the superposing-averaging processing can be done for a number of adjacent cycle selected along the time axis in either a forward direction, a backward direction, or both. No matter which directions is selected, the restored waveforms are similar, but the number of cycles (N) for superposing-averaging should be a constant for all the processing. If N is big enough (8 or 16), the respiration interference and other interferences will be well cancelled during the processing, while those cyclically repeated features in the impedance rheographic component, which are useful for diagnostic purposes, will be enhanced and become more distinguishable after the in-phase superposing-averaging processing, thus the required useful information is obtained.

Figure 4:
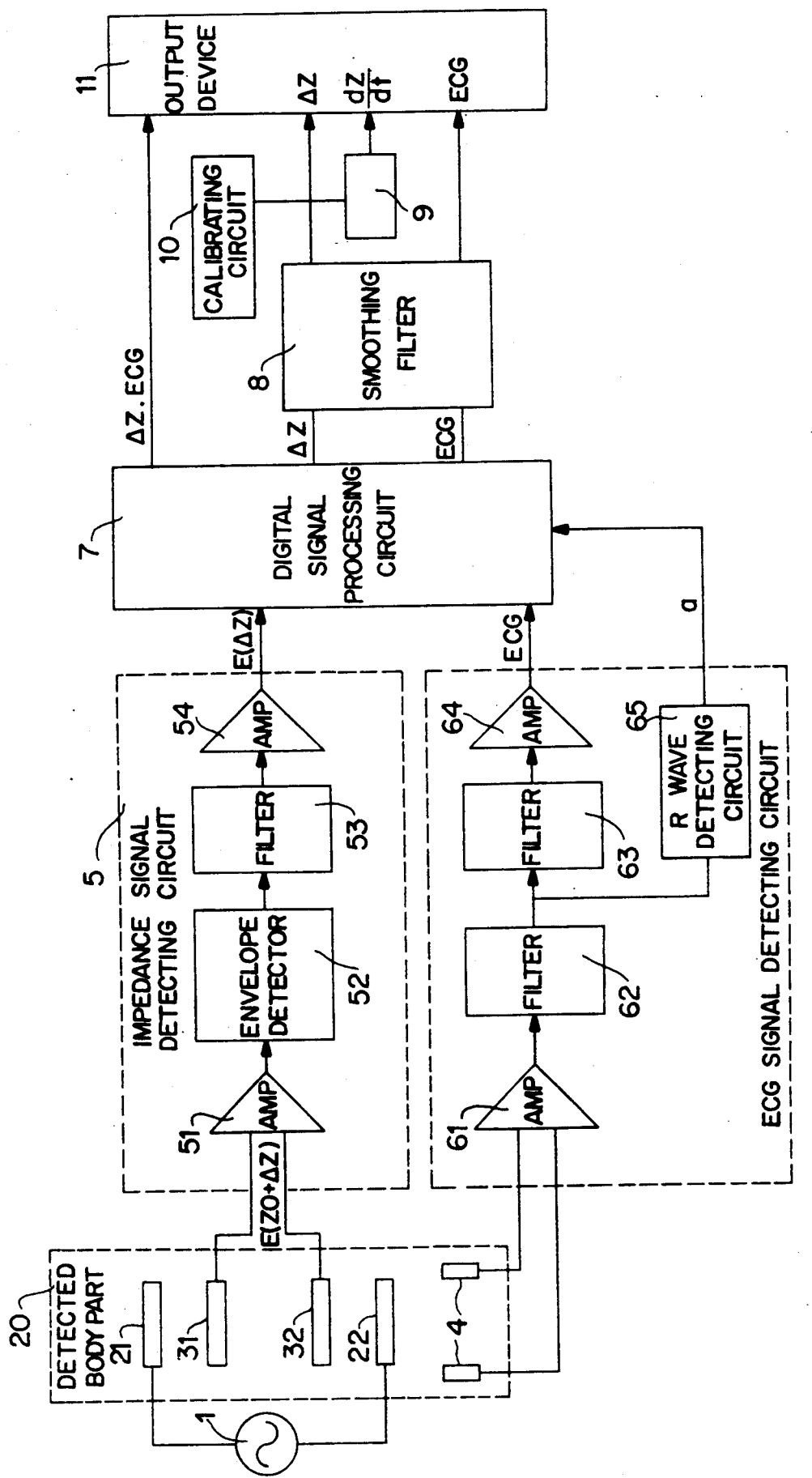
FIG. 4 shows an illustrating block diagram of an embodiment of the apparatus according to the present invention.

Referring to FIG. 4, there is shown the block diagram of one embodiment of the apparatus according to the present invention. Numeral 1 indicates a constant current source which generates a constant current of a frequency in the range of 20–100 $KH_z$ and an amplitude of less than 2 mA, the preferred frequency thereof being 50 $KH_z$ or 100 $KH_z$. The constant current source 1 provides the constant current to a detected body part represented by a dashed line block 20 via a pair of current output electrodes 21 and 22, and at the same time, a pair of voltage detecting electrodes indicated by numerals 31 and 32 detect a voltage signal E $(Z_o + \Delta Z)$ which represents the impedance value at the part, wherein Z represents the impedance variation by respiration and the change of blood volume. The impedance signal is amplified and filtered by an impedance signal detecting circuit indicated by a dashed line block 5. The detecting circuit 5 comprises a high frequency amplifying circuit 51 which is fulfilled by a conventional bioelectric signal amplifier which provides its output signal to an envelope detector 52 which is fulfilled by a conventional accurate small signal linear envelope detector which detects the envelope of the high frequency impedance signal and provides the same as output to a low-pass filtering circuit 53 for filtering 50 $H_z$ operating frequency (50 Hz) interference and other higher frequency interference. Because the impedance signal is a low-frequency one, the cut-off frequency of the low-pass filtering circuit 53 is preferably selected as about 30 Hz. The impedance signal after the low-pass filtering proveded to a low-frequency amplifying circuit 54 for amplifying it to a level adequate for later A/D converting.

In FIG. 4 the numeral 4 indicates a set of ECG detecting electrodes, the dashed line block 6 represents an ECG signal detecting circuit which detects, via electrode 4, at least one lead of the ECG signals which, on the one hand, is used as a reference signal in the processing of the impedance signal, and on the other hand, is provided synchronously with the processed impedance signal as the final output to be used by doctors for diagnostic purposes. The ECG signal detecting circuit 6 comprises a high-frequency amplifying circuit 61 which is fulfilled by a conventional high input impedance bioelectric signal amplifier which provides an output to 50 Hz band elimination filter 62 for filtering operating frequency interference, then the signal passes a low-pass filtering circuit 63 for filtering the high-frequency interference coming from the constant current source 1 and other high-frequency interferences. The cut-off frequency of the low-pass filtering circuit 63 may be selected as about 100 Hz. The filtered ECG signal is amplified by an amplifying circuit 64 to a level adequate for later A/D converting. The output of the band elimination filter 62 is also provided to an R wave detecting circuit 65 which is made up of a differential amplifier and a monostable trigger for detecting from the ECG signal a pulse sequence corresponding to the R waves to be used in later digital processing. The outputs of the impedance signal detecting circuit 5 and the ECG signal detecting circuit 6 are input parallel to and processed in a digital signal processing circuit 7. The structure and operation of the circuit 7 may refer to FIG. 5, 6 and 7, respectively, and their corresponding descriptions.

It should be pointed out that during the operation of the apparatus, the impedance signal E $(Z_o + Z)$ and the ECG signal are detected simultaneously so as to guarantee synchronized processing of these parallel signals by the digital signal processing circuit 7. After being processed by the circuit 7, the impedance and ECG signals are either provided synchronously as digital output, or converted into analog form and provided to the output device 12 via a smoothing filter 8. The impedance signal may also be provided to a differential circuit 11 to produce a differential impedance signal dZ/dt. In FIG. 4, a calibrating circuit 10 is used to calibrate the impedance output. Since these circuits are known in the art, they will not be further described.

Figure 5:
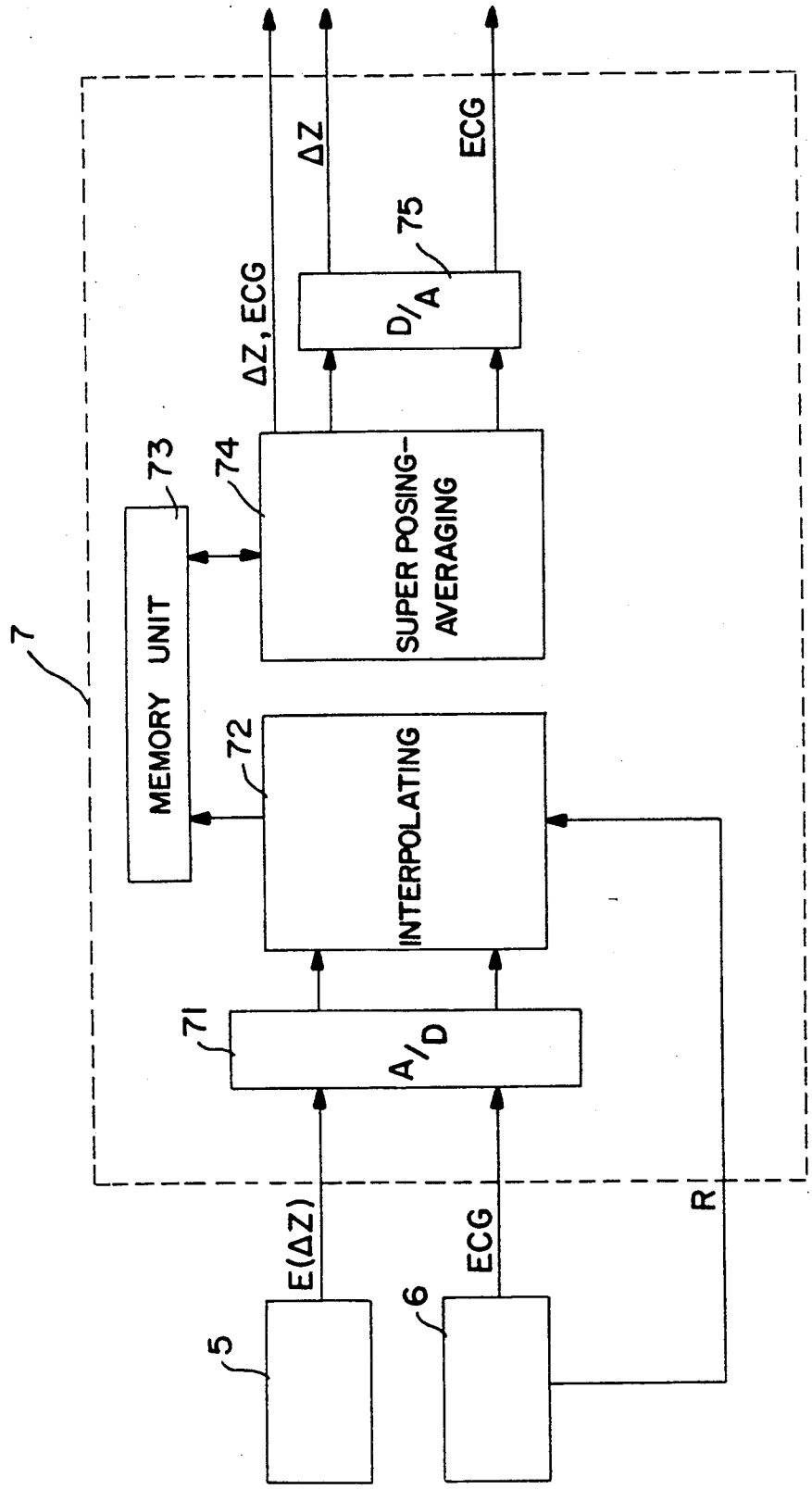
FIG. 5 shows an illustrating block diagram of the digital signal processing circuit 7 shown in FIG. 4.

FIG. 5 shows a block diagram of the digital signal processing circuit 7 shown in FIG. 4. The circuit 7 comprises an A/D converter 71 for synchronously converting the impedance signal ($\Delta Z$) from the impedance signal detecting circuit 5 and the ECG signal from the ECG signal detecting circuit 6 into digital form, then providing them to an interpolation processing unit 72 for further processing. The unit 72 also inputs from the ECG signal detecting circuit 6 the R wave sequence for dividing the impedance signal into cycles so that the linear interpolation processing can be performed for the sampled impedance and ECG signals according to the sampling results of each cycle, and the processed results are stored in a memory unit 73. When a predetermined number of cycles of interpolating results are stored in the memory unit 73, a superposing-averaging processing unit 74 performs in-phase superposing-averaging processing on the stored data, then restores the waveform of the impedance signal according to interpolating points of each cycle. As the unit 72, continuously supplies new interpolating results to the memory unit 73, the superposing-averaging processing unit 74 continuously provides the output of impedance waveform restored in new cycles, then the impedance waveform and ECG signal are provided in digital form for further data processing, external storing and/or displaying, and may also be converted into analog form by a D/A converter 75 for output. The above processing units 72 and 74 can be fulfilled by any conventional computer device, the programs executed by them being shown respectively in FIG. 6 and 7. It can be seen from the above descriptions that the processing unit 72 performs linear interpolation processing for both the impedance signal and the ECG signal, but the processing unit 74 only performs in-phase superposing-averaging processing to the impedance signal the purpose of such an arrangement is to maintain the two parallel signals synchronized, so that the final outputs of the two waveforms will keep their original corresponding time relationship, which is useful to doctors.

Figure 6:
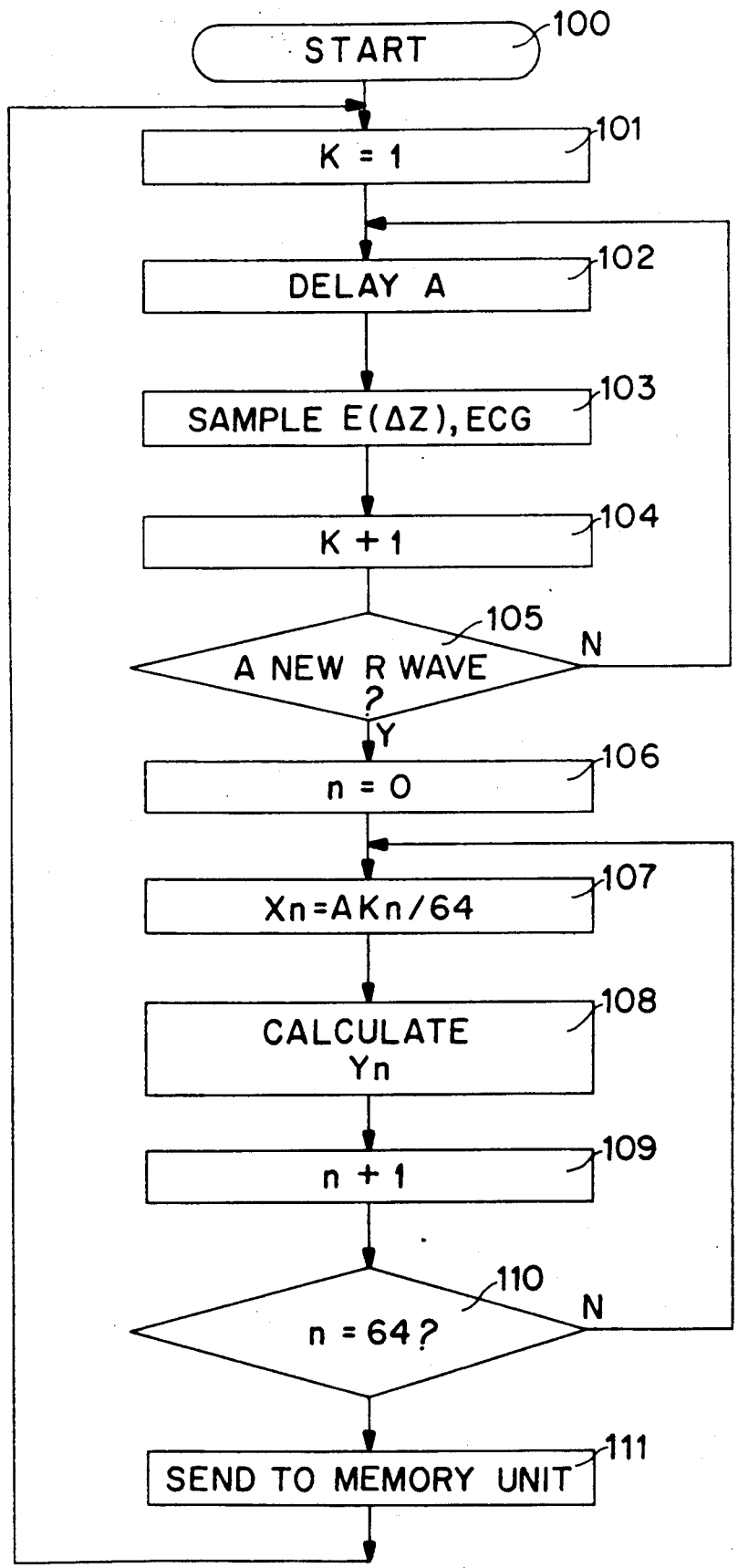
FIG. 6 shows the flow chart of the linear interpolation program executed by the interpolation processing unit 72 shown in FIG. 5.

Refer to FIG. 6, there is shown a flow chart of the linear interpolation processing program executed by the interpolation processing unit 72 shown in FIG. 5. The program starts at step 100, where the rising edge of an R wave from the ECG signal detecting circuit 6 is used as the start point of a cycle, and the impedance and ECG signals are sampled according to a constant sampling interval A (A is preferably 10 mS). At step 101, the sampling count K for this cycle is as 1, then it is delayed for a predetermined time A at step 102. The signal E ($\Delta Z$) and the ECG signal are sampled once with the sampled values registered at step 103, then the sampling count K is incremented by 1 at step 104. Next, at step 105, it is judged whether there is a new R wave. If not, the program returns to step 102 to sample the next point and the program repeats in the same way until it is judged at step 105 that a new R wave appears, whereby the sampling of an entire cardiac cycle has been conducted. Then the program enters step 106 to set the interpolating number n as zero and begins the interpolation processing for this cycle. At step 107, the abscissa of the nth interpolating point is calculated according to the constant sampling interval A and the sampling count K for this cycle, then the amplitude $Y_n$ of the impedance signal corresponding to this interpolating point is calculated according to the above-mentioned equation (2) at step 108. The interpolating number n is incremented by 1 at step 109, and the program enters step 110 to judge whether n is 64. If n is less than 64, then the interpolating process has not yet been finished for this cycle, and the program returns to step 107 to continue interpolating until n is 64, which means that all 64 interpolating points for this cycle have been calculated. Then, at step 111 the calculated results are sent to the memory unit and the program returns to step 101 to start the same process for a new cycle. It should be pointed out that in the program shown by FIG. 6, the number of interpolating points for one cycle is predetermined as 64. If the number of interpolating points for one cycle is changed to 128, the relevent amendments should be made for the equation at step 107 and judgement at step 110. After the processed results of this program have been sent to the memory unit, as in-phase superposing-averaging process can be performed.

Figure 7:
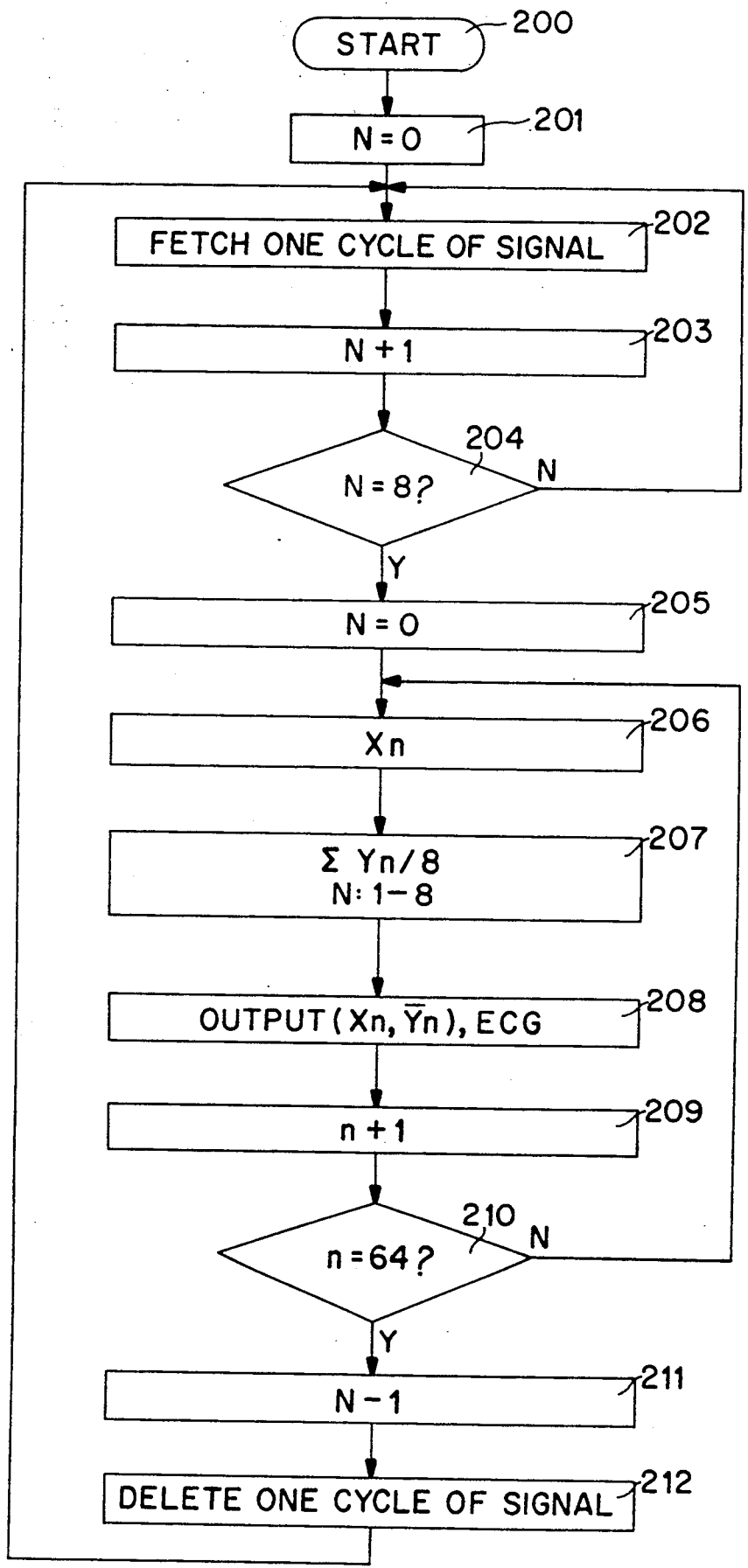
FIG. 7 shows the flow chart of the superposing-averaging program executed by the superposing-averaging processing unit 74 shown in FIG. 5.

FIG. 7 shows a flow chart of the in-phase superposing-averaging processing program executed by the processing unit 74 shown in FIG. 5 wherein, the program starts at step 200. First the superposing number N is set to zero at step 201. At step 202, a cycle of impedance signal is fetched from the memory unit, and the number N is incremented by step 1 at step 203. Then, it is judged at step 204 whether N is 8, if N is less than 8, which means that not enough cycles of a signal have been fetched, the program returns to step 202 for fetching the signal of the next cycle, until N equals 8, which means 8 cycles of continuous impedance signal have been fetched, and the program advances to step 205 where the interpolating number n is set as zero. Then, the abscissa $X_n$ of the nth interpolating point is determined at step 206. At step 207, the corresponding impedance values $Y_n$ in all 8 cycles are superposed and averaged to obtain an averaged value $Y_n$. Then at step 208, the coordinates ($X_n$, $Y_n$) of the impedance waveform and their synchronized ECG data are provided as outputs. Next, at step 209 the number n is incremented by 1 then it is judged at step 210 whether n is equal to 64. If n is less than 64 which means the superposing and averaging for the whole cycle have not been finished, then the program returns to step 206 for processing the next point, until n is increased to 64, which means the processing for the entire cycle has been conducted. At step 211 the superposing number N is subtracted by 1, then at step 212, the data of the first cycle of 8 successively fetched cycles are eliminated and the program returns to step 202 for fetching a new cycle of data from the memory unit, on the processing according to a new group of 8 cycles of signals begins. By using the program shown in FIG. 7, the impedance waveform of one cycle is provided as output after the processing has been conducted and the same process will go on until the operator inputs the instruction to stop. The superposing number in this program is 8, but the operator can preset any other number (for example, 16), then the judgement at step 204 is changed. In addition the number 64 at step 210 is the interpolating number in the program shown in FIG. 6, and if it is changed to 128 in FIG. 6, it should also be changed at step 210 in FIG. 7, accordingly.

Heretofore, the structure and operation of one embodiment of the apparatus and method according to the present invention have been fully described. Obviously, many modifications and rearrangements can be made to the disclosed embodiment by those skilled in the art without departing from the spirit and scope of the present invention. Therefore, the scope of the present invention will by no means be limited to this exemplary embodiment, and will only be determined by the accompanying claims.

What is claimed is:

1. An apparatus for detecting and processing an impedance rheogram, comprising:
    a constant current source for generating a constant current having a frequency range of 20-100 KHz and an amplitude of less than 2 mA;
    a pair of output electrodes connected to said constant current source for applying the constant current to a subject's body part;
    a pair of voltage detecting electrodes for detecting from said body part of voltage signal which represents a change of impedance in response to the constant current applied to the said body part;
    means for detecting an impedance signal from said voltage detecting electrodes and for further amplifying and filtering the impedance signal detected thereby;
    ECG signal detecting electrodes adapted to be connected to the said body part for detecting an ECG signal generated by the said body part;
    means for detecting the ECG signal generated by said ECG signal detecting electrodes, for amplifying and filtering the ECG signal detected, and for generating an R wave sequence from the ECG signal;
    digital signal processing means connected to an output of each said means for detecting said impedance signal and said means for detecting said ECG signal wherein said impedance signal, ECG signal and R wave sequence are connected in parallel to said digital signal processing means; and
    an output device connected to said digital signal processing means for displaying and recording the impedance signal and ECG signal;
    wherein said digital signal processing means performs A/D converting and sampling of said impedance and ECG signals, divides said impedance signal into cycles according to said R wave sequence and performs linear interpolating processing within each cycle, said linear interpolation processing including selection of a predetermined number of interpolating points for each cycle, subsequently performs in-phase superposing-averaging processing of the impedance signal for a predetermined number of cycles and restores the impedance signal according to the interpolating points, and synchronously outputs the impedance and ECG signals to said output device.

2. The apparatus as claimed by claim 1, wherein said impedance signal detecting means includes a high frequency amplifier connected to said voltage detecting electrodes, an envelope detector connected to an output of said high frequency amplifier, a low-pass filter connected to an output of said envelope detector, and a low frequency amplifier connected to an output of said low-pass filter for providing an adequate level impedance signal, wherein the cut-off frequency of said low-pass filter is about 30 Hz to filter the high frequency interference in said impedance signal.

3. The apparatus as claimed in claim 1, wherein said ECG signal detecting means includes a high frequency amplifier connected to said ECG detecting electrodes, a band elimination filter connected to an output of said high frequency amplifier for filtering an operating frequency interference, a low-pass filter having a cut-off frequency of 100 Hz connected to an output of said band elimination filter, a low frequency amplifier connected to an output of said low-pass filter for providing an ECG signal of adequate level, and an R wave detector connected to an output of said band elimination filter for generating an R wave sequence.

4. The apparatus as claimed by claim 1, wherein said digital signal processing means includes and A/D converter connected to outputs of said impedance signal detecting means and ECG signal detecting means for synchronously converting said impedance signal and ECG signal into respective digital signal, interpolation processing means which samples said digital impedance and ECG signals at constant time intervals and divides said impedance signal into cycles according to said R wave sequence input from said ECG signal detecting means, then performs linear interpolation processing within each cycle for a predetermined number of points, a memory unit connected to an output of said interpolation processing means for storing interpolation results, superposing-averaging processing means which fetches a predetermined number of continuous cycles of interpolating results from said memory unit and conducts in-phase superposing-averaging processing thereon and restores the impedance waveform according to the predetermined number of interpolating points, and a D/A converter connected to an output of said superposing-averaging processing means for converting an output impedance waveform and synchronized ECG waveform into respective analog signals for parallel output.

5. The apparatus as claimed in claim 4, wherein said interpolation processing means performs 64 or 128 points of interpolation processing in each cycle and said superposing-averaging processing means performs superposing on 8 or 16 cycles.

6. The apparatus as claimed in claim 1, further comprising:
    a smoothing filter connected to analog outputs of said digital signal processing means for smoothly filtering the impedance and ECG signals;
    a calibrating circuit connected to an impedance output of said smoothing filter for calibrating its output signal; and
    a differential circuit connected to the impedance output of said smoothing filter for generating the differential signal of said impedance signal;
    wherein said smoothing filter, calibrating circuit and differential circuit are connected in parallel to said output device for displaying and recording the impedance and ECG signals.

7. The apparatus as claimed in claim 1, wherein each of said cycles may be of a different length according to said R wave sequence and sampling at said constant time interval will cause an actual number of samplings per cycle to vary according to the length of the cycle.

8. A method for detecting and processing impedance rheogram comprising the steps of:

1) applying a constant current having a frequency in the range of 20–100 KHz and an amplitude of less than 2mA to a part of a subject's body;
2) detecting a voltage variation caused by a change of impedance of said body part under the effect of said constant current and using said voltage variation as an impedance signal;
3) simultaneously detecting the subject's ECG signal and generating a R waveform sequence therefrom;
4) synchronously converting said impedance signal and ECG signal into respective digital signals and sampling the same at constant time intervals;
5) dividing said sampled impedance signal into cycles according to rising edges of said R wave sequence and conducting in each cycle a linear interpolation for a predetermined number of interpolation points;
6) performing in-phase superposing-averaging for a predetermined number of cycles of an interpolated impedance signal and restoring an impedance waveform according to said interpolating points; and
7) displaying and recording said impedance waveform and synchronized ECG waveform via an output device.

9. The method as claimed in claim 8, wherein said predetermined number of points in step 5) is 64 or 128 and said predetermined number of cycles in step 6) is 8 or 16.

* * * * *